United States Patent
Kalnes et al.

(10) Patent No.: US 7,915,460 B2
(45) Date of Patent: Mar. 29, 2011

(54) PRODUCTION OF DIESEL FUEL FROM BIORENEWABLE FEEDSTOCKS WITH HEAT INTEGRATION

(75) Inventors: Tom N. Kalnes, LaGrange, IL (US); John P. Brady, Algonquin, IL (US); Marco Di Stanislao, Desio (IT)

(73) Assignees: UOP LLC, Des Plaines, IL (US); ENI S.p.A., Rome (IT)

( * ) Notice: Subject to any disclaimer, the term of this patent is extended or adjusted under 35 U.S.C. 154(b) by 401 days.

(21) Appl. No.: 12/193,170

(22) Filed: Aug. 18, 2008

(65) Prior Publication Data

US 2009/0077865 A1    Mar. 26, 2009

Related U.S. Application Data

(60) Provisional application No. 60/973,795, filed on Sep. 20, 2007.

(51) Int. Cl.
    *C10G 1/00*    (2006.01)
(52) U.S. Cl. .................. 585/240; 585/266; 585/638
(58) Field of Classification Search .................. 585/240, 585/266, 638
    See application file for complete search history.

(56) References Cited

U.S. PATENT DOCUMENTS

| | | | |
|---|---|---|---|
| 5,186,722 A | 2/1993 | Cantrell et al. | |
| 5,705,722 A | 1/1998 | Monnier et al. | |
| 7,232,935 B2 | 6/2007 | Jakkula et al. | |
| 7,279,018 B2 | 10/2007 | Jakkula et al. | |
| 7,288,685 B2 * | 10/2007 | Marker .................. | 585/240 |
| 7,425,657 B1 | 9/2008 | Elliott et al. | |
| 7,459,597 B2 | 12/2008 | Koivusalmi et al. | |
| 7,491,858 B2 * | 2/2009 | Murzin et al. ................. | 585/240 |
| 7,501,546 B2 | 3/2009 | Koivusalmi et al. | |
| 7,511,181 B2 * | 3/2009 | Petri et al. .................... | 585/240 |
| 7,540,952 B2 | 6/2009 | Pinho et al. | |
| 7,550,634 B2 * | 6/2009 | Yao et al. ...................... | 585/240 |
| 2006/0186020 A1 | 8/2006 | Gomes | |
| 2006/0207166 A1 | 9/2006 | Herskowitz et al. | |
| 2007/0006523 A1 | 1/2007 | Myllyoja et al. | |
| 2007/0010682 A1 | 1/2007 | Myllyoja et al. | |
| 2007/0068848 A1 | 3/2007 | Monnier et al. | |
| 2007/0131579 A1 | 6/2007 | Koivusalmi et al. | |
| 2007/0135316 A1 | 6/2007 | Koivusalmi et al. | |
| 2007/0135663 A1 | 6/2007 | Aalto et al. | |
| 2007/0161832 A1 | 7/2007 | Myllyoja et al. | |
| 2007/0170091 A1 | 7/2007 | Monnier et al. | |
| 2007/0175795 A1 | 8/2007 | Yao et al. | |
| 2007/0260102 A1 | 11/2007 | Duarte Santiago et al. | |
| 2007/0281875 A1 | 12/2007 | Scheibel et al. | |

(Continued)

FOREIGN PATENT DOCUMENTS

CN    11270300 A    9/2008

(Continued)

*Primary Examiner* — N. Bhat
(74) *Attorney, Agent, or Firm* — Maryann Maas

(57) ABSTRACT

A process has been developed for producing diesel boiling range fuel or fuel blending component from renewable feedstocks such as plant oils and greases. The process involves treating a renewable feedstock by hydrogenating and deoxygenating i.e. decarboxylating and/or hydrodeoxygenating to provide a hydrocarbon fraction useful as a diesel fuel. The hydrocarbon fraction is isomerized to improve cold flow properties. At least one interstage stream of the hydrogenating and deoxygenating reaction zone is heat exchanged with the feed to the isomerization reaction zone, and/or the effluent of the hydrogenating and deoxygenating reaction zone is heat exchanged with the feed to the isomerization reaction zone.

15 Claims, 4 Drawing Sheets

U.S. PATENT DOCUMENTS

| | | |
|---|---|---|
| 2007/0287873 A1 | 12/2007 | Coupard et al. |
| 2007/0299291 A1 | 12/2007 | Koivusalmi |
| 2008/0025903 A1 | 1/2008 | Cortright |
| 2008/0033188 A1 | 2/2008 | Dumesic et al. |
| 2008/0045731 A1 | 2/2008 | Zhang |
| 2008/0050792 A1 | 2/2008 | Zmierczak et al. |
| 2008/0052983 A1 | 3/2008 | Aulich et al. |
| 2008/0066374 A1 | 3/2008 | Herskowitz |
| 2008/0092436 A1 | 4/2008 | Seames et al. |
| 2008/0132435 A1 | 6/2008 | Ferreira Fontes et al. |
| 2008/0156694 A1 | 7/2008 | Chapus et al. |
| 2008/0161614 A1 | 7/2008 | Bertoncini et al. |
| 2008/0161615 A1 | 7/2008 | Chapus et al. |
| 2008/0163543 A1 | 7/2008 | Abhari et al. |
| 2008/0173570 A1 | 7/2008 | Marchand et al. |
| 2008/0216391 A1 | 9/2008 | Cortright et al. |
| 2008/0229654 A1 | 9/2008 | Bradin |
| 2008/0244962 A1 | 10/2008 | Abhari et al. |
| 2008/0281134 A1 | 11/2008 | Ghonasgi et al. |
| 2008/0300434 A1 | 12/2008 | Cortright et al. |
| 2008/0300435 A1 | 12/2008 | Cortright et al. |
| 2008/0302001 A1 | 12/2008 | Koivusalmi et al. |
| 2008/0308457 A1 | 12/2008 | Dindi et al. |
| 2008/0308458 A1 | 12/2008 | Dindi et al. |
| 2008/0312480 A1 | 12/2008 | Dindi et al. |
| 2008/0313955 A1 | 12/2008 | Silva et al. |
| 2009/0014354 A1 | 1/2009 | Knuuttila et al. |
| 2009/0019763 A1 | 1/2009 | Ghonasgi et al. |
| 2009/0029427 A1 | 1/2009 | Miller |
| 2009/0031617 A1 | 2/2009 | O'Rear |
| 2009/0062578 A1 | 3/2009 | Koivusalmi et al. |
| 2009/0069610 A1 | 3/2009 | Roberts, IV et al. |
| 2009/0071872 A1 | 3/2009 | Ginosar et al. |
| 2009/0077864 A1 | 3/2009 | Marker et al. |
| 2009/0077866 A1 | 3/2009 | Kalnes et al. |
| 2009/0077867 A1 | 3/2009 | Marker et al. |
| 2009/0077868 A1 | 3/2009 | Brady et al. |
| 2009/0078611 A1 | 3/2009 | Marker et al. |
| 2009/0082603 A1 | 3/2009 | Kalnes et al. |
| 2009/0082606 A1 | 3/2009 | Marker et al. |
| 2009/0084026 A1 | 4/2009 | Miller |
| 2009/0088351 A1 | 4/2009 | Miller |
| 2009/0107033 A1 | 4/2009 | Gudde et al. |
| 2009/0124839 A1 | 5/2009 | Dumesic et al. |
| 2009/0126260 A1 | 5/2009 | Aravanis et al. |
| 2009/0193709 A1 | 8/2009 | Marker et al. |

FOREIGN PATENT DOCUMENTS

| | | |
|---|---|---|
| CN | 11343552 A | 1/2009 |
| EP | 1719811 A1 | 8/2006 |
| EP | 2046917 | 1/2008 |
| WO | 2007063874 A1 | 6/2007 |
| WO | 2007064015 A1 | 6/2007 |
| WO | 2007064019 A1 | 6/2007 |
| WO | WO 2007/064019 A1 | 6/2007 |
| WO | WO 2007/063874 A1 | 6/2007 |
| WO | WO 2007/064015 A1 | 6/2007 |
| WO | 2007125332 A1 | 11/2007 |
| WO | WO 2007/125332 A1 | 11/2007 |
| WO | 2007141293 A1 | 12/2007 |
| WO | WO 2007/141293 A1 | 12/2007 |
| WO | 2008012415 A2 | 1/2008 |
| WO | WO 2008/012415 A2 | 1/2008 |
| WO | 2008020048 A2 | 2/2008 |
| WO | WO 2008/020048 A2 | 2/2008 |
| WO | 2008053284 A1 | 5/2008 |
| WO | WO 2008/053284 A1 | 5/2008 |
| WO | 2008101945 A1 | 8/2008 |
| WO | WO 2008/101945 A1 | 8/2008 |
| WO | 2008105518 A1 | 9/2008 |
| WO | 2008119895 A2 | 9/2008 |
| WO | WO 2008/105518 A1 | 9/2008 |
| WO | WO 2008/119895 A2 | 9/2008 |
| WO | 2008141830 A1 | 11/2008 |
| WO | 2008141831 A1 | 11/2008 |
| WO | WO 2008/141830 A1 | 11/2008 |
| WO | WO 2008/141831 A1 | 11/2008 |
| WO | 2008151792 A1 | 12/2008 |
| WO | 2008152199 A1 | 12/2008 |
| WO | WO 2008/151792 A1 | 12/2008 |
| WO | WO 2008/152199 A1 | 12/2008 |
| WO | 2009004181 A2 | 1/2009 |
| WO | 2009011639 A2 | 1/2009 |
| WO | 2009013233 A2 | 1/2009 |
| WO | WO 2009/004181 A2 | 1/2009 |
| WO | WO 2009/011639 A2 | 1/2009 |
| WO | WO 2009/013233 A2 | 1/2009 |
| WO | 2009025542 A1 | 2/2009 |
| WO | WO 2009/020055 A1 | 2/2009 |
| WO | WO 2009/025542 A1 | 2/2009 |
| WO | 2009059819 A1 | 5/2009 |
| WO | 2009059920 A2 | 5/2009 |
| WO | WO 2009/059819 A1 | 5/2009 |
| WO | WO 2009/059920 A2 | 5/2009 |

\* cited by examiner

US 7,915,460 B2

PRODUCTION OF DIESEL FUEL FROM BIORENEWABLE FEEDSTOCKS WITH HEAT INTEGRATION

CROSS-REFERENCE TO RELATED APPLICATION

This application claims priority from Provisional Application Ser. No. 60/973,795 filed Sep. 20, 2007, the contents of which are hereby incorporated by reference in its entirety.

FIELD OF THE INVENTION

This invention relates to a process for producing hydrocarbons useful as diesel boiling range fuel from renewable feedstocks such as the glycerides and free fatty acids found in materials such as plant and animal fats and oils. The process involves a deoxygenation zone followed by an isomerization zone. In one embodiment, the deoxygenation zone has at least two stages and the interstage stream is heat exchanged with the stream entering the isomerization zone. In another embodiment, the effluent of the deoxygenation zone is heat exchanged with the stream entering the isomerization zone.

BACKGROUND OF THE INVENTION

As the demand for diesel boiling range fuel increases worldwide there is increasing interest in sources other than petroleum crude oil for producing diesel fuel. One such source is what has been termed renewable sources. These renewable sources include, but are not limited to, plant oils such as corn, rapeseed, canola, soybean and algal oils, animal fats such as inedible tallow, fish oils and various waste streams such as yellow and brown greases and sewage sludge. The common feature of these sources is that they are composed of glycerides and Free Fatty Acids (FFA). Both of these classes of compounds contain aliphatic carbon chains having from about 8 to about 24 carbon atoms. The aliphatic chains in the glycerides or FFAs can also be mono, di or poly-unsaturated.

There are reports in the art disclosing the production of hydrocarbons from oils. For example, U.S. Pat. No. 4,300,009 discloses the use of crystalline aluminosilicate zeolites to convert plant oils such as corn oil to hydrocarbons such as gasoline and chemicals such as para-xylene. U.S. Pat. No. 4,992,605 discloses the production of hydrocarbon products in the diesel boiling range by hydroprocessing vegetable oils such as canola or sunflower oil. Finally, US 2004/0230085 A1 discloses a process for treating a hydrocarbon component of biological origin by hydrodeoxygenation followed by isomerization.

Applicants have developed a process which comprises deoxygenating and isomerizing the renewable feedstock and incorporates heat integration to reduce costs. In one embodiment, the deoxygenation is performed in at least two stages. The deoxygenation reaction is exothermic and to minimize energy consumption, the interstage stream of the deoxygenation zone is heat exchanged with the stream introduced to the isomerization zone. In another embodiment having a significant recycle stream to the deoxygenation zone, the effluent of the deoxygenation zone is heat exchanged with the stream introduced to the isomerization zone.

SUMMARY OF THE INVENTION

A conversion process for producing an isoparaffin-rich diesel product from a renewable feedstock wherein the process comprises treating the feedstock in a catalytic first reaction zone by hydrogenating and deoxygenating the feedstock at reaction conditions to provide a first reaction product comprising a hydrocarbon fraction comprising n-paraffins. The carbon dioxide and water generated as byproducts in the first reaction zone are removed from the first reaction product in an integrated a hot high pressure hydrogen stripper using high purity hydrogen as the stripping gas. The hydrogen stripped first reaction product is introduced to a second reaction zone, a hydroisomerization reaction zone. The isomerized product is recovered. In one embodiment, the interstage fluid of the first reaction zone is heat exchanged with the fluid entering the second reaction zone. In another embodiment, a portion of the hydrogen stripped first reaction product is recycled to the first reaction zone, the deoxygenation zone, and the effluent of the first reaction zone is heat exchanged with the fluid entering the second reaction zone. In yet another embodiment, the first reaction zone comprises at least two beds, and a portion of the hydrogen stripped first reaction product is recycled to the first reaction zone. Both the interstage stream of the first reaction zone and the effluent of the first reaction zone are heat exchanged with the stream entering the second reaction zone.

BRIEF DESCRIPTION OF THE DRAWINGS

FIG. 1 is a more simplistic schematic, while FIG. 2 is more detailed.

FIG. 3 is a more simplistic schematic, while FIG. 4 is more detailed.

DETAILED DESCRIPTION OF THE INVENTION

Figure 1:
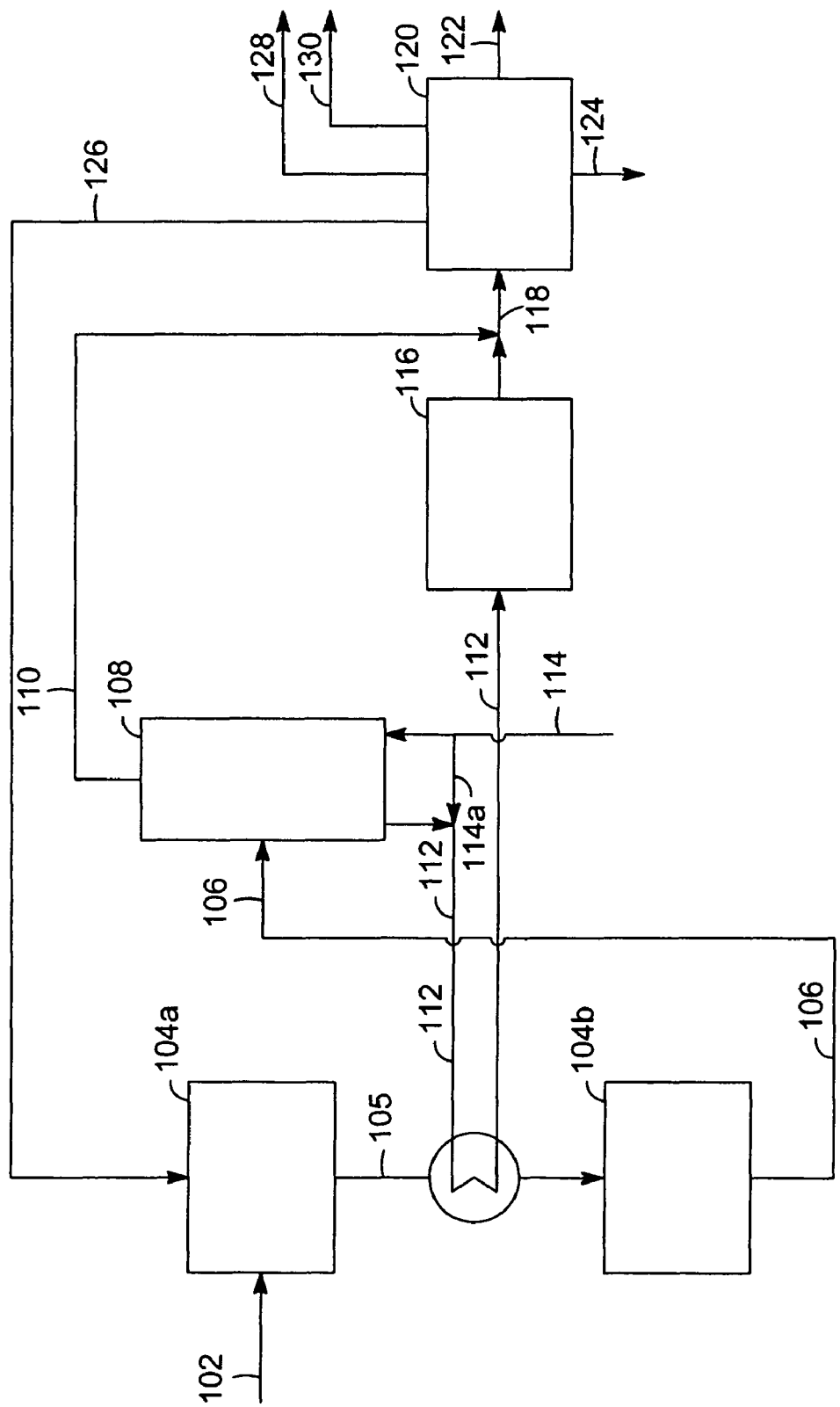
FIG. 1 and FIG. 2 are schematics of one embodiment of the invention wherein the Interstage fluid of the first reaction zone is heat exchanged with the fluid entering the second reaction zone.

As stated, the present invention relates to a process for producing a hydrocarbon stream useful as diesel fuel from renewable feedstocks such as those originating from plants or animals. The term renewable feedstock is meant to include feedstocks other than those obtained from petroleum crude oil. Another term that has been used to describe this class of feedstock is biorenewable fats and oils. The renewable feedstocks that can be used in the present invention include any of those which comprise glycerides and free fatty acids (FFA). Most of the glycerides will be triglycerides, but monoglycerides and diglycerides may be present and processed as well. Examples of these renewable feedstocks include, but are not limited to, canola oil, corn oil, soy oils, rapeseed oil, soybean oil, colza oil, tall oil, sunflower oil, hempseed oil, olive oil, linseed oil, coconut oil, castor oil, peanut oil, palm oil, mustard oil, jatropha oil, tallow, yellow and brown greases, lard, train oil, fats in milk, fish oil, algal oil, sewage sludge, and the like. Additional examples of renewable feedstocks include non-edible vegetable oils from the group comprising Jatropha curcas (Ratanjoy, Wild Castor, Jangli Erandi), Madhuca indica (Mohuwa), Pongamia pinnata (Karanji Honge), and Azadiracta indicia (Neem). The triglycerides and FFAs of the typical vegetable or animal fat contain aliphatic hydrocarbon chains in their structure which have about 8 to about 24 carbon atoms with a majority of the fats and oils containing high concentrations of fatty acids with 16 and 18 carbon atoms. Mixtures or co-feeds of renewable feedstocks and petroleum derived hydrocarbons may also be used as the feedstock. Other feedstock components which may be used, especially as a co-feed component in combination with the above listed feedstocks, include spent motor oils and industrial lubricants, used paraffin waxes, liquids derived from the gasification of coal, biomass, or natural gas followed by a downstream liquefaction step such as Fischer-Tropsch technology, liquids derived from depolymerization, thermal or chemical, of waste plastics such as polypropylene, high density polyethylene, and low density polyethylene; and other synthetic oils generated as byproducts from petrochemical and chemical processes. Mixtures of the above feedstocks may also be used as co-feed components. One advantage of using a co-feed component is the transformation of what has been considered to be a waste product from a petroleum based or other process into a valuable co-feed component to the current process.

Renewable feedstocks that can be used in the present invention may contain a variety of impurities. For example, tall oil is a byproduct of the wood processing industry and tall oil contains esters and rosin acids in addition to FFAs. Rosin acids are cyclic carboxylic acids. The renewable feedstocks may also contain contaminants such as alkali metals, e.g. sodium and potassium, phosphorous as well as solids, water and detergents. An optional first step is to remove as much of these contaminants as possible. One possible pretreatment step involves contacting the renewable feedstock with an ion-exchange resin in a pretreatment zone at pretreatment conditions. The ion-exchange resin is an acidic ion exchange resin such as Amberlyst™-15 and can be used as a bed in a reactor through which the feedstock is flowed through, either upflow or downflow. The conditions at which the reactor is operated are well known in the art.

Another possible means for removing contaminants is a mild acid wash. This is carried out by contacting the feedstock with an acid such as sulfuric, nitric or hydrochloric acid in a reactor. The acid and feedstock can be contacted either in a batch or continuous process. Contacting is done with a dilute acid solution usually at ambient temperature and atmospheric pressure. If the contacting is done in a continuous manner, it is usually done in a counter current manner. Yet another possible means of removing metal contaminants from the feedstock is through the use of guard beds which are well known in the art. These can include alumina guard beds either with or without demetallation catalysts such as nickel or cobalt. Filtration and solvent extraction techniques are other choices which may be employed. Hydroprocessing such as that described in U.S. application Ser. No. 11/770,826, hereby incorporated by reference, is another pretreatment technique which may be employed.

The renewable feedstock is flowed to a first reaction zone comprising one or more catalyst beds in two or more reactors. The term "feedstock" is meant to include feedstocks that have not been treated to remove contaminants as well as those feedstocks purified in a pretreatment zone. In the first reaction zone, the feedstock is contacted with a hydrogenation or hydrotreating catalyst in the presence of hydrogen at hydrogenation conditions to hydrogenate the olefinic or unsaturated portions of the aliphatic chains. Hydrogenation and hydrotreating catalysts are any of those well known in the art such as nickel or nickel/molybdenum dispersed on a high surface area support. Other hydrogenation catalysts include one or more noble metal catalytic elements dispersed on a high surface area support. Non-limiting examples of noble metals include Pt and/or Pd dispersed on gamma-alumina. Hydrogenation conditions include a temperature of about 40° C. to about 400° C. and a pressure of about 689 kPa absolute (100 psia) to about 13,790 kPa absolute (2000 psia). In another embodiment the hydrogenation conditions include a temperature of about 200° C. to about 300° C. and a pressure of about 1379 kPa absolute (200 psia) to about 4826 kPa absolute (700 psia). Other operating conditions for the hydrogenation zone are well known in the art.

The hydrogenation catalysts enumerated above are also capable of catalyzing decarboxylation, decarbonylation, and/or hydrodeoxygenation of the feedstock to remove oxygen. Decarboxylation, decarbonylation, and hydrodeoxygenation are herein collectively referred to as deoxygenation reactions. Decarboxylation conditions include a relatively low pressure of about 3447 kPa (500 psia) to about 6895 kPa (1000 psia), a temperature of about 200° C. to about 400° C. and a liquid hourly space velocity of about 0.5 to about 10 hr$^{-1}$. In another embodiment the decarboxylation conditions include the same relatively low pressure of about 3447 kPa (500 psia) to about 6895 kPa (1000 psia), a temperature of about 288° C. to about 345° C. and a liquid hourly space velocity of about 1 to about 4 hr$^{-1}$. Since hydrogenation is an exothermic reaction, as the feedstock flows through the catalyst bed the temperature increases and decarboxylation, decarbonylation, and hydrodeoxygenation will begin to occur. Thus, it is envisioned and is within the scope of this invention that all of the can reactions occur simultaneously in each reactor although the relative proportion of each reaction occurring may change across the reaction zone.

Due to the exothermic nature of the reactions, without heat removal, reaction zone temperatures would be excessive causing undesirable formation of high molecular weight polymers and coke which can lead to premature catalyst deactivation and increased production of light hydrocarbon gases such as methane. Conventional heat removal techniques include both gas and liquid quench streams. However, solutions that minimize energy consumption are preferred. Therefore, in one embodiment, the first reaction zone is divided into at least two sections and heat generated from the exothermic hydrogenation and deoxygenation reactions is recovered from between the two sections and transferred to the isomerization reaction zone inlet. In another embodiment where the product from the first reaction zone is recycled to the first reaction zone, heat is recovered from the effluent of the first reaction zone and transferred to the isomerization reaction zone inlet. In still another embodiment where the product from the first reaction zone is recycled to the first reaction zone, heat is recovered from at least one interstage stream and the effluent of the reaction zone and is transferred to the fluid entering the isomerization zone. Recovery of heat in this manner can provide both a means of controlling the first reaction zone temperature rise and a means of heating the isomerization reaction zone feed downstream. This feature is particularly important in light of the selective separation step downstream of the first reaction zone, but upstream of the isomerization reaction zone, which operates at a lower temperature than either reaction zone. In addition, trace oxygenates and other high molecular weight intermediates in the first reaction zone effluent will not be converted to lower molecular weight paraffins and branched paraffins in the isomerization reaction zone if the temperature is too low. Cooling the reaction zone effluent stream below the melting point of these byproducts before they are fully converted can lead to fouling of equipment and contamination of the water byproduct product stream. This heat integration eliminates the need for a fired heater upstream of the isomerization zone and additional consumption of fuel in this heater, both of which are economically and environmentally undesirable.

The reaction product from the deoxygenation reactions will comprise a liquid portion and a gaseous portion. The liquid portion comprises a hydrocarbon fraction which is essentially all n-paraffins and having a large concentration of paraffins in the range of about 9 to about 18 carbon atoms. Different feedstocks will result in different distributions of paraffins. The gaseous portion comprises hydrogen, carbon dioxide, carbon monoxide, water vapor, propane and perhaps sulfur components such as hydrogen sulfide or phosphorous component such as phosphine. As hydrogen is an expensive resource, to conserve costs, the hydrogen is separated and recycled to the deoxygenation reactor. The effluent from the deoxygenation reactor is conducted to a hot high pressure hydrogen stripper. One purpose of the hot high pressure hydrogen stripper is to separate the gaseous portion of the effluent from the liquid portion of the effluent. Failure to remove the water, carbon monoxide, and carbon dioxide may result in poor catalyst performance in the isomerization zone. Water, carbon monoxide, carbon dioxide, any ammonia or hydrogen sulfide are selectively stripped using make-up hydrogen as the stripping gas. The temperature may be controlled in a limited range to achieve the desired separation and the pressure may be maintain at approximately the same pressure as the two reaction zones to minimize both investment and operating costs. The hot high pressure hydrogen stripper may be operated at conditions ranging from a pressure of about 689 kPa absolute (100 psia) to about 13,790 kPa absolute (2000 psia), and a temperature of about 40° C. to about 350° C. In another embodiment the hot high pressure hydrogen stripper may be operated at conditions ranging from a pressure of about 1379 kPa absolute (200 psia) to about 4826 kPa absolute (700 psia), or about 2413 kPa absolute (350 psia) to about 4882 kPa absolute (650 psia), and a temperature of about 50° C. to about 350° C.

The effluent enters the hot high pressure hydrogen stripper and the gaseous components are carried with the hydrogen stripping gas and separated into an overhead stream. Additional hydrogen is used as the stripping gas. The remainder of the deoxygenation effluent stream is removed as hot high pressure hydrogen stripper bottoms and contains the liquid hydrocarbon fraction having components such as normal hydrocarbons having from about 8 to about 24 carbon atoms. A portion of this liquid hydrocarbon fraction in hot high pressure hydrogen stripper bottoms may be used as the hydrocarbon recycle described below.

Hydrogen is a reactant in the reactions above, and to be effective, a sufficient quantity of hydrogen must be in solution to most effectively take part in the catalytic reaction. Past processes have operated at high pressures in order to achieve a desired amount of hydrogen in solution and readily available for reaction. However, higher pressure operations are more costly to build and to operate as compared to their lower pressure counterparts. One advantage of the present invention is the operating pressure may be in the range of about 1379 kPa absolute (200 psia) to about 4826 kPa absolute (700 psia) which is lower than that found in other previous operations. In another embodiment the operating pressure is in the range of about 2413 kPa absolute (350 psia) to about 4481 kPa absolute (650 psia), and in yet another embodiment operating pressure is in the range of about 2758 kPa absolute (400 psia) to about 4137 kPa absolute (600 psia). Furthermore, the rate of reaction is increased resulting in a greater amount of throughput of material through the reactor in a given period of time.

The desired amount of hydrogen is kept in solution at lower pressures by employing a larger recycle of hydrocarbon. Other processes have employed hydrocarbon recycle in order to control the temperature in the reaction zones since the reactions are exothermic reactions. However, the range of recycle to feedstock ratios used herein is determined not on temperature control requirements, but instead, based upon hydrogen solubility requirements. Hydrogen has a greater solubility in the hydrocarbon product than it does in the feedstock. By utilizing a large hydrocarbon recycle the solubility of hydrogen in the liquid phase in the reaction zone is greatly increased and higher pressures are not needed to increase the amount of hydrogen in solution. In one embodiment of the invention, the volume ratio of hydrocarbon recycle to feedstock is from about 2:1 to about 8:1 or about 2:1 to about 6:1. In another embodiment the ratio is in the range of about 3:1 to about 6:1 and in yet another embodiment the ratio is in the range of about 4:1 to about 5:1.

Although this hydrocarbon fraction is useful as a diesel fuel, because it comprises essentially n-paraffins, it will have poor cold flow properties. If it is desired to improve the cold flow properties of the liquid hydrocarbon fraction, then the entire reaction product can be contacted with an isomerization catalyst under isomerization conditions to at least partially isomerize the n-paraffins to branched paraffins. The effluent of the second reaction zone, the isomerization zone, is a branched paraffin-rich stream. By the term "rich" it is meant that the effluent stream has a greater concentration of branched paraffins than the stream entering the isomerization zone, and preferably comprises greater than 50 mass-% branched paraffins. It is envisioned that the isomerization zone effluent may contains 70, 80, or 90 mass-% branched paraffins. Isomerization can be carried out in a separate bed of the same reaction zone, i.e. same reactor, described above or the isomerization can be carried out in a separate reactor. For ease of description the following will address the embodiment where a second reactor is employed for the isomerization reaction. The hydrocarbon stream is contacted with an isomerization catalyst in the presence of hydrogen at isomerization conditions to isomerize the normal paraffins to branched paraffins. Only minimal branching is required, enough to overcome the cold-flow problems of the normal paraffins. Since attempting for significant branching runs the risk of high degree of undesired cracking, the predominant isomerized product is a mono-branched hydrocarbon.

The isomerization of the paraffinic product can be accomplished in any manner known in the art or by using any suitable catalyst known in the art. See for example US 2004/0230085 A1 which is incorporated by reference in its entirety. Suitable catalysts comprise a metal of Group VIII (IUPAC 8-10) of the Periodic Table and a support material. Suitable Group VIII metals include platinum and palladium, each of which may be used alone or in combination. The support material may be amorphous or crystalline. Suitable support materials include amorphous alumina, amorphous silica-alumina, ferrierite, ALPO-31, SAPO-11, SAPO-31, SAPO-37, SAPO-41, SM-3, MgAPSO-31, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MeAPSO-11, MeAPSO-31, MeAPSO-41, MeAPSO-46, ELAPO-11, ELAPO-31, ELAPO-41, ELAPSO-11, ELAPSO-31, ELAPSO-41, laumontite, cancrinite, offretite, hydrogen form of stillbite, magnesium or calcium form of mordenite, and magnesium or calcium form of partheite, each of which may be used alone or in combination. ALPO-31 is described in U.S. Pat. No. 4,310,440. SAPO-11, SAPO-31, SAPO-37, and SAPO-41 are described in U.S. Pat. No. 4,440,871. SM-3 is described in U.S. Pat. No. 4,943,424; U.S. Pat. No. 5,087,347; U.S. Pat. No. 5,158,665; and U.S. Pat. No. 5,208,005. MgAPSO is a MeAPSO, which is an acronym for a metal aluminumsilicophosphate molecular sieve, where the metal Me is magnesium (Mg). Suitable MeAPSO-31 catalysts include MgAPSO-31. MeAPSOs are described in U.S. Pat. No. 4,793,984, and MgAPSOs are described in U.S. Pat. No. 4,758,419. MgAPSO-31 is a preferred MgAPSO, where 31 means a MgAPSO having structure type 31. Many natural zeolites, such as ferrierite, that have an initially reduced pore size can be converted to forms suitable for olefin skeletal isomerization by removing associated alkali metal or alkaline earth metal by ammonium ion exchange and calcination to produce the substantially hydrogen form, as taught in U.S. Pat. No. 4,795,623 and U.S. Pat. No. 4,924,027. Further catalysts and conditions for skeletal isomerization are disclosed in U.S. Pat. No. 5,510,306, U.S. Pat. No. 5,082,956, and U.S. Pat. No. 5,741,759.

The isomerization catalyst may also comprise a modifier selected from the group consisting of lanthanum, cerium, praseodymium, neodymium, samarium, gadolinium, terbium, and mixtures thereof, as described in U.S. Pat. No. 5,716,897 and U.S. Pat. No. 5,851,949. Other suitable support materials include ZSM-22, ZSM-23, and ZSM-35, which are described for use in dewaxing in U.S. Pat. No. 5,246,566 and in the article entitled "New molecular sieve process for lube dewaxing by wax isomerization," written by S. J. Miller, in Microporous Materials 2 (1994) 439-449. The teachings of U.S. Pat. No. 4,310,440; U.S. Pat. No. 4,440,871; U.S. Pat. No. 4,793,984; U.S. Pat. No. 4,758,419; U.S. Pat. No. 4,943,424; U.S. Pat. No. 5,087,347; U.S. Pat. No. 5,158,665; U.S. Pat. No. 5,208,005; U.S. Pat. No. 5,246,566; U.S. Pat. No. 5,716,897; and U.S. Pat. No. 5,851,949 are hereby incorporated by reference.

U.S. Pat. No. 5,444,032 and U.S. Pat. No. 5,608,968 teach a suitable bifunctional catalyst which is constituted by an amorphous silica-alumina gel and one or more metals belonging to Group VIIIA, and is effective in the hydroisomerization of long-chain normal paraffins containing more than 15 carbon atoms. U.S. Pat. No. 5,981,419 and U.S. Pat. No. 5,908,134 teach a suitable bifunctional catalyst which comprises: (a) a porous crystalline material isostructural with beta-zeolite selected from boro-silicate (BOR—B) and boro-aluminosilicate (Al—BOR—B) in which the molar $SiO_2:Al_2O_3$ ratio is higher than 300:1; (b) one or more metal(s) belonging to Group VIIIA, selected from platinum and palladium, in an amount comprised within the range of from 0.05 to 5% by weight. Article V. Calemma et al., App. Catal. A: Gen., 190 (2000), 207 teaches yet another suitable catalyst.

The isomerization catalyst may be any of those well known in the art such as those described and cited above. Isomerization conditions include a temperature of about 150° C. to about 360° C. and a pressure of about 1724 kPa absolute (250 psia) to about 4726 kPa absolute (700 psia). In another embodiment the isomerization conditions include a temperature of about 300° C. to about 360° C. and a pressure of about 3102 kPa absolute (450 psia) to about 3792 kPa absolute (550 psia). Other operating conditions for the isomerization zone are well known in the art. The operating pressure of the isomerization zone is at a pressure at least 345 kPa absolute (50 psia) greater than that of the first reaction zone. In the event that a leak develops in the heat exchangers, the higher pressure of the isomerization zone will prevent the effluent of the deoxygenation zone from entering the isomerization zone before the carbon dioxide is removed from the deoxygenation zone effluent. The isomerization zone catalyst is sensitive to carbon dioxide and should a leak develop in the heat exchangers, it is preferable to have the higher pressure of the isomerization zone force isomerization zone feed into the deoxygenation zone effluent as opposed to contaminating the isomerization zone feed with carbon dioxide from the raw deoxygenation zone effluent.

The final effluent stream, i.e. the stream obtained after all reactions have been carried out, is now processed through one or more separation steps to obtain a purified hydrocarbon stream useful as a diesel boiling range fuel, or fuel blending component. With the final effluent stream comprising both a liquid component and a gaseous component, various portions of which are to be recycled, multiple separation steps may be employed. For example, hydrogen can be first separated in a isomerization effluent separator with the separated hydrogen being removed in an overhead stream. Suitable operating conditions of the isomerization effluent separator include, for example, a temperature of 230° C. and a pressure of 4100 kPa absolute (600 psia). If there is a low concentration of carbon oxides, or the carbon oxides are removed, the hydrogen may be recycled back to the hot high pressure hydrogen stripper for use as a stripping gas. The remainder of the final effluent after the removal of hydrogen still has liquid and gaseous components and is cooled, by techniques such as air cooling or water cooling and passed to a cold separator where the liquid component is separated from the gaseous component. Suitable operating conditions of the cold separator include, for example, a temperature of about 20 to 60° C. and a pressure of 3850 kPa absolute (560 psia). A water byproduct stream is also separated.

The liquid component contains the hydrocarbons useful as diesel boiling range fuel, or fuel blending component as well as smaller amounts of naphtha and LPG. The separated liquid component may be recovered as diesel fuel or it may be further purified in a product stripper which separates lower boiling components and dissolved gases from the diesel product containing C8 to C24 normal and mono-branched alkanes. Suitable operating conditions of the product stripper include a temperature of from about 20 to about 200° C. at the overhead and a pressure from about 0 to about 1379 kPa absolute (0 to 200 psia).

The LPG/Naphtha stream may be further separated in a debutanizer or depropanizer in order to separate the LPG into an overhead stream, leaving the naphtha in a bottoms stream. Suitable operating conditions of this unit include a temperature of from about 20 to about 200° C. at the overhead and a pressure from about 0 to about 2758 kPa absolute (0 to 400 psia). The LPG may be sold as valuable product or may be used as feed to a hydrogen production facility. Similarly, the naphtha may be used as feed to a hydrogen or gasoline production facility, or used as a fuel blending component in for example, the gasoline blending pool.

The gaseous component separated in the product separator comprises mostly hydrogen and the carbon dioxide from the decarboxylation reaction. Other components such as carbon monoxide, propane, and hydrogen sulfide or other sulfur containing component may be present as well. It is desirable to recycle the hydrogen to the isomerization zone, but if the carbon dioxide was not removed, its concentration would quickly build up and effect the operation of the isomerization zone. The carbon dioxide can be removed from the hydrogen absorption with an amine, reaction with a hot carbonate solution, pressure swing absorption, etc. If desired, essentially pure carbon dioxide can be recovered by regenerating the spent absorption media.

Similarly, a sulfur containing component such as hydrogen sulfide may be present to maintain the sulfided state of the deoxygenation catalyst or to control the relative amounts of the decarboxylation reaction and the hydrogenation reaction that are both occurring in the deoxygenation zone. The amount of sulfur is generally controlled and so must be removed before the hydrogen is recycled. The sulfur components may be removed using techniques such as absorption with an amine or by caustic wash. Of course, depending upon the technique used, the carbon dioxide and sulfur containing components, and other components, may be removed in a single separation step such as a hydrogen selective membrane.

The hydrogen remaining after the removal of at least carbon dioxide may be recycled to the reaction zone where hydrogenation primarily occurs and/or to any subsequent beds/reactors. The recycle stream may be introduced to the inlet of the reaction zone and/or to any subsequent beds/reactors. One benefit of the hydrocarbon recycle is to control the temperature rise across the individual beds. However, as discussed above, the amount of hydrocarbon recycle may be determined based upon the desired hydrogen solubility in the reaction zone which is in excess of that used for temperature control. Increasing the hydrogen solubility in the reaction mixture allows for successful operation at lower pressures, and thus reduced cost.

The following embodiment is presented in illustration of this invention and is not intended as an undue limitation on the generally broad scope of the invention as set forth in the claims. First, one embodiment of the process is described in general with reference to FIG. 1. Then the same embodiment is described in more detail with reference to FIG. 2. Another embodiment of the process is described in general with reference to FIG. 3 and then in detail with reference to FIG. 4.

Turning to FIG. 1 renewable feedstock 102 enters deoxygenation reaction zone 104 along with recycle hydrogen 126. Deoxygenated product 106 is stripped in hot hydrogen stripper 108 using hydrogen 114*a*. Carbon oxides and water vapor are removed with hydrogen in overhead 110. Stripped deoxygenated product is passed to isomerization zone 116 along with make-up hydrogen 114*b*. Isomerized product 118 is combined with overhead 110 and passed to product recovery zone 120. Carbon oxide stream 128, light ends stream 130, water byproduct stream 124, hydrogen stream 126, and branched paraffin-rich product 122 are removed from product recover zone 120. Branched paraffin-rich product 122 may be collected for use as diesel fuel and hydrogen stream 128 is recycled to both the deoxygenation reaction zone 104 and isomerization zone 116.

Figure 2:
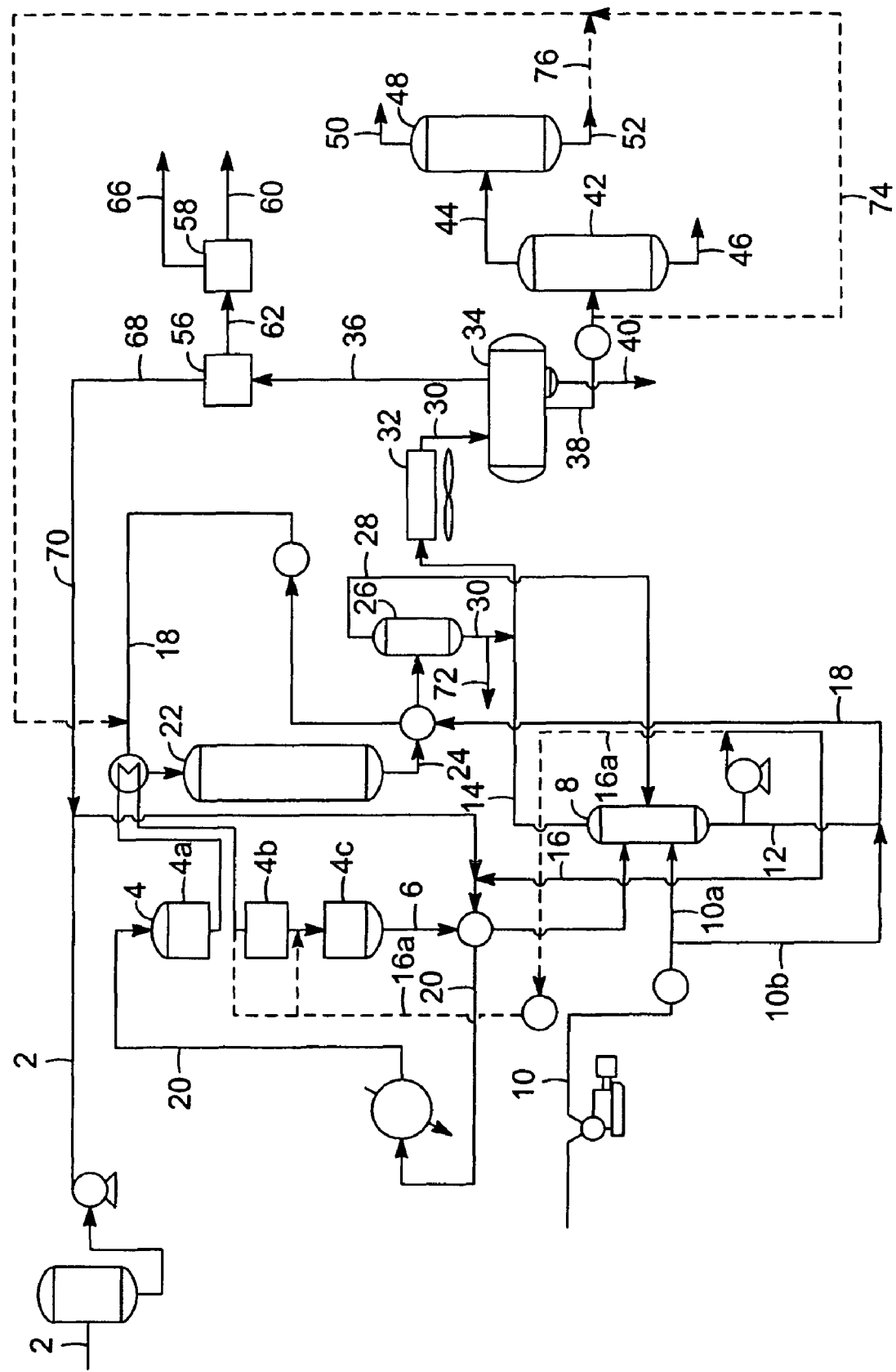

Turning to FIG. 2, the process begins with a renewable feedstock stream 2 which may pass through an optional feed surge drum. The feedstock stream is combined with recycle stream 16 to form combined feed stream 20, which is heat exchanged with the deoxygenation zone effluent and then introduced into deoxygenation reactor 4. The heat exchange may occur before or after the recycle is combined with the feed. Deoxygenation reactor 4 may contain multiple beds as shown in FIG. 1 as 4*a*, 4*b* and 4*c*. The multiple beds may be connected using a conduit such as interstage conduit 5 which provides fluid communication between bed 4*a* and bed 4*b*. Deoxygenation reactor 4 contains at least one catalyst capable of catalyzing decarboxylation and/or hydrodeoxygenation of the feedstock to remove oxygen. Because the deoxygenation reactions are exothermic, excess heat generated may be transferred to a stream needing to be heated, thereby conserving energy and costs. Interstage conduit 5 containing the products of the decarboxylation and/or hydrodeoxygenation reactions of bed 4*a* is heat exchanged with stream 18 which is being fed to the isomerization zone reactor.

Deoxygenation reactor effluent stream 6, which comprises a liquid component containing largely normal paraffin hydrocarbons in the diesel boiling range and a gaseous component containing largely hydrogen, vaporous water, carbon monoxide, carbon dioxide and propane, is directed to hot high pressure hydrogen stripper 8. Make up hydrogen in line 10 is divided into two portions, stream 10*a* and 10*b*. Make up hydrogen in stream 10*a* is also introduced to hot high pressure hydrogen stripper 8. In hot high pressure hydrogen stripper 8, the gaseous component of deoxygenation reactor effluent 6 is stripped from the liquid component of deoxygenation reactor effluent 6 using make-up hydrogen 10*a* and recycle hydrogen 28. The gaseous component comprising hydrogen, vaporous water, carbon monoxide, carbon dioxide and possibly some propane, is separated into hot high pressure hydrogen stripper overhead stream 14. The remaining liquid component of deoxygenation reactor effluent 6 comprising primarily normal paraffins having a carbon number from about 8 to about 24 with a cetane number of about 60 to about 100 is removed as hot high pressure hydrogen stripper bottom 12.

A portion of hot high pressure hydrogen stripper bottoms forms recycle stream 16 and is combined with renewable feedstock stream 2 to create combined feed 20. Another portion of recycle stream 16, optional stream 16*a*, may be routed directly to deoxygenation reactor 4 and introduced at interstage locations such as between beds 4*a* and 4*b* and/or between beds 4*b* and 4*c* in order, or example, to aid in temperature control. The remainder of hot high pressure hydrogen stripper bottoms in stream 12 is combined with hydrogen stream 10*b* to form combined stream 18 which is routed to isomerization reactor 22. Stream 18 may be heat exchanged with isomerization reactor effluent 24.

The product of the isomerization reactor containing a gaseous portion of hydrogen and propane and a branched paraffin-rich liquid portion is removed in line 24, and after optional heat exchange with stream 18, is introduced into hydrogen separator 26. The overhead stream 28 from hydrogen separator 26 contains primarily hydrogen which may be recycled back to hot high pressure hydrogen stripper 8. Bottom stream 30 from hydrogen separator 26 is air cooled using air cooler 32 and introduced into product separator 34. In product separator 34 the gaseous portion of the stream comprising hydrogen, carbon monoxide, hydrogen sulfide, carbon dioxide and propane are removed in stream 36 while the liquid hydrocarbon portion of the stream is removed in stream 38. A water byproduct stream 40 may also be removed from product separator 34. Stream 38 is introduced to product stripper 42 where components having higher relative volatilities are separated into stream 44 with the remainder, the diesel boiling range components, being withdrawn from product stripper 42 in line 46. Stream 44 is introduced into fractionator 48 which operates to separate LPG into overhead 50 leaving a naphtha bottoms 52.

The vapor stream 36 from product separator 34 contains the gaseous portion of the isomerization effluent which comprises at least hydrogen, carbon monoxide, hydrogen sulfide, carbon dioxide and propane and is directed to a system of amine absorbers to separate carbon dioxide and hydrogen sulfide from the vapor stream. Because of the cost of hydrogen, it is desirable to recycle the hydrogen to deoxygenation reactor 4, but it is not desirable to circulate the carbon dioxide or an excess of sulfur containing components. In order to separate sulfur containing components and carbon dioxide from the hydrogen, vapor stream 36 is passed through a system of at least two amine absorbers, also called scrubbers, starting with the first amine absorber zone 56. The amine chosen to be employed in first amine scrubber 56 is capable of selectively removing at least both the components of interest, carbon dioxide and the sulfur components such as hydrogen sulfide. Suitable amines are available from DOW and from BASF, and in one embodiment the amines are a promoted or activated methyldiethanolamine (MDEA). The promoter may be piperazine, and the promoted amine may be used as an aqueous solution. See U.S. Pat. No. 6,337,059, hereby incorporated by reference in its entirety. Suitable amines for the first amine absorber zone from DOW include the UCARSOL™ AP series solvents such as AP802, AP804, AP806, AP810 and AP814. The carbon dioxide and hydrogen sulfide are absorbed by the amine while the hydrogen passes through first amine scrubber zone and into line 68 to be recycled to the first reaction zone. The amine is regenerated and the carbon dioxide and hydrogen sulfide are released and removed in line 62. Within the first amine absorber zone, regenerated amine may be recycled for use again. The released carbon dioxide and hydrogen sulfide in line 62 are passed through second amine scrubber zone 58 which contains an amine selective to hydrogen sulfide, but not selective to carbon dioxide. Again, suitable amines are available from DOW and from BASF, and in one embodiment the amines are a promoted or activated MDEA. Suitable amines for the second amine absorber zone from DOW include the UCARSOL™ HS series solvents such as HS101, HS102, HS103, HS104, HS115. Therefore the carbon dioxide passes through second amine scrubber zone 58 and into line 66. The amine may be regenerated which releases the hydrogen sulfide into line 60. Regenerated amine is then reused.

Figure 3:
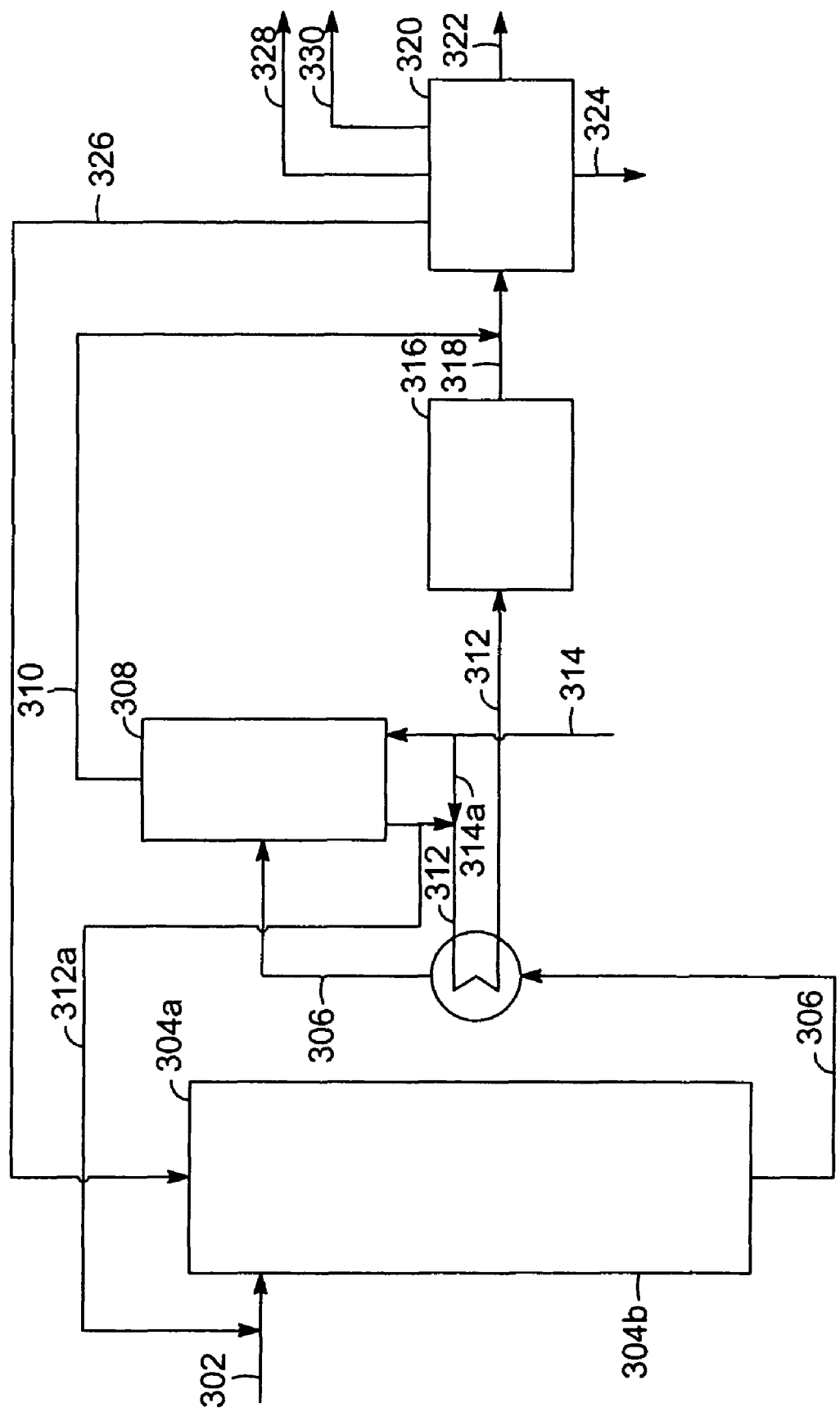
FIG. 3 and FIG. 4 are schematics of one embodiment of the invention wherein the effluent of the first reaction zone is heat exchanged with the fluid entering the second reaction zone.

Turning to FIG. 3 renewable feedstock 302 enters deoxygenation reaction zone 304 along with recycle hydrogen 326 and recycle deoxygenated product 312*a*. Deoxygenated product 306 is heat exchanged with stripped deoxygenated product 312 and introduced to hot high pressure hydrogen stripper 308 where it is stripped using hydrogen 314*a*. Carbon oxides and water vapor are removed with hydrogen in overhead 310. Stripped deoxygenated product 312 is passed to isomerization zone 316 along with make-up hydrogen 314*a*. Isomerized product 318 is combined with overhead 310 and passed to product recovery zone 320. Carbon oxide stream 328, light ends stream 330, water byproduct stream 324, hydrogen stream 326, and branched paraffin-rich product 322 are removed from product recover zone 320. Branched paraffin-rich product 322 may be collected for use as diesel fuel and hydrogen stream 328 is recycled to both the deoxygenation reaction zone 304 and isomerization zone 316.

Figure 4:
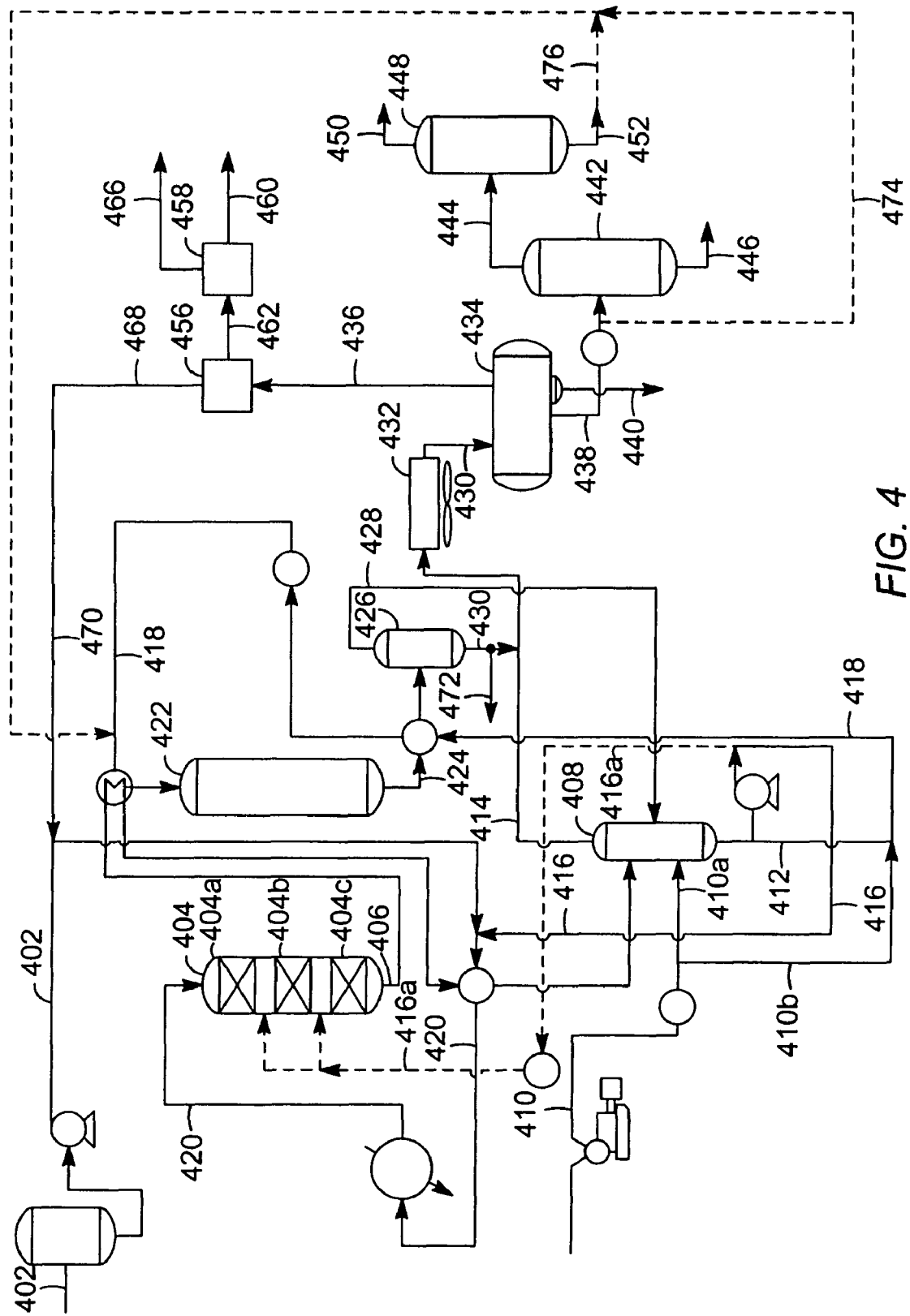

Turning to FIG. 4, the process begins with a renewable feedstock stream 402 which may pass through an optional feed surge drum. The feedstock stream is combined with recycle stream 416 to form combined feed stream 420, which is heat exchanged with the deoxygenation zone effluent and then introduced into deoxygenation reactor 404. The heat exchange may occur before or after the recycle is combined with the feed. Deoxygenation reactor 404 may contain multiple beds as shown in FIG. 1 as 404*a*, 404*b* and 404*c*. Deoxygenation reactor 404 contains at least one catalyst capable of catalyzing decarboxylation and/or hydrodeoxygenation of the feedstock to remove oxygen. Because the deoxygenation reactions are exothermic, excess heat generated may be transferred to a stream needing to be heated, thereby conserving energy and costs. Effluent 406 containing the products of the decarboxylation and/or hydrodeoxygenation reaction beds is heat exchanged with stream 418 which is being fed to the isomerization zone reactor.

Deoxygenation reactor effluent stream 406, which comprises a liquid component containing largely normal paraffin hydrocarbons in the diesel boiling range and a gaseous component containing largely hydrogen, vaporous water, carbon monoxide, carbon dioxide and propane, is directed to hot high pressure hydrogen stripper 408. Make up hydrogen in line 410 is divided into two portions, stream 410*a* and 410*b*. Make up hydrogen in stream 410*a* is also introduced to hot high pressure hydrogen stripper 408. In hot high pressure hydrogen stripper 408, the gaseous component of deoxygenation reactor effluent 406 is stripped from the liquid component of deoxygenation reactor effluent 406 using make-up hydrogen 410*a* and recycle hydrogen 428. The gaseous component comprising hydrogen, vaporous water, carbon monoxide, carbon dioxide and possibly some propane, is separated into hot high pressure hydrogen stripper overhead stream 414. The remaining liquid component of deoxygenation reactor effluent 406 comprising primarily normal paraffins having a carbon number from about 8 to about 24 with a cetane number of about 60 to about 100 is removed as hot high pressure hydrogen stripper bottom 412.

A portion of hot high pressure hydrogen stripper bottoms forms recycle stream 416 and is combined with renewable feedstock stream 402 to create combined feed 420. Another portion of recycle stream 416, optional stream 416*a*, may be routed directly to deoxygenation reactor 404 and introduced at interstage locations such as between beds 404*a* and 404*b* and/or between beds 404*b* and 404*c* in order, or example, to aid in temperature control. The remainder of hot high pressure hydrogen stripper bottoms in stream 412 is combined with hydrogen stream 410*b* to form combined stream 418 which is routed to isomerization reactor 422. Stream 418 may be heat exchanged with isomerization reactor effluent 424.

The product of the isomerization reactor containing a gaseous portion of hydrogen and propane and a branched paraffin-rich liquid portion is removed in line 424, and after optional heat exchange with stream 418, is introduced into hydrogen separator 426. The overhead stream 428 from hydrogen separator 426 contains primarily hydrogen which may be recycled back to hot high pressure hydrogen stripper 408. Bottom stream 30 from hydrogen separator 426 is air cooled using air cooler 432 and introduced into product separator 434. In product separator 434 the gaseous portion of the stream comprising hydrogen, carbon monoxide, hydrogen sulfide, carbon dioxide and propane are removed in stream 436 while the liquid hydrocarbon portion of the stream is removed in stream 438. A water byproduct stream 40 may also be removed from product separator 434. Stream 438 is introduced to product stripper 442 where components having higher relative volatilities are separated into stream 444 with the remainder, the diesel range components, being withdrawn from product stripper 442 in line 446. Stream 444 is introduced into fractionator 448 which operates to separate LPG into overhead 450 leaving a naphtha bottoms 452.

The vapor stream 436 from product separator 434 contains the gaseous portion of the isomerization effluent which comprises at least hydrogen, carbon monoxide, hydrogen sulfide, carbon dioxide and propane and is directed to a system of amine absorbers to separate carbon dioxide and hydrogen sulfide from the vapor stream. Because of the cost of hydrogen, it is desirable to recycle the hydrogen to deoxygenation reactor 404, but it is not desirable to circulate the carbon dioxide or an excess of sulfur containing components. In order to separate sulfur containing components and carbon dioxide from the hydrogen, vapor stream 36 is passed through a system of at least two amine absorbers, also called scrubbers, starting with the first amine absorber zone 456. The amine chosen to be employed in first amine scrubber 456 is capable of selectively removing at least both the components of interest, carbon dioxide and the sulfur components such as hydrogen sulfide. Suitable amines are available from DOW and from BASF, and in one embodiment the amines are a promoted or activated methyldiethanolamine (MDEA). The promoter may be piperazine, and the promoted amine may be used as an aqueous solution. See U.S. Pat. No. 6,337,059, hereby incorporated by reference in its entirety. Suitable amines for the first amine absorber zone from DOW include the UCARSOL™ AP series solvents such as AP802, AP804, AP806, AP810 and AP814. The carbon dioxide and hydrogen sulfide are absorbed by the amine while the hydrogen passes through first amine scrubber zone and into line 68 to be recycled to the first reaction zone. The amine is regenerated and the carbon dioxide and hydrogen sulfide are released and removed in line 462. Within the first amine absorber zone, regenerated amine may be recycled for use again. The released carbon dioxide and hydrogen sulfide in line 462 are passed through second amine scrubber zone 58 which contains an amine selective to hydrogen sulfide, but not selective to carbon dioxide. Again, suitable amines are available from DOW and from BASF, and in one embodiment the amines are a promoted or activated MDEA. Suitable amines for the second amine absorber zone from DOW include the UCARSOL™ HS series solvents such as HS101, HS102, HS103, HS104, HS115. Therefore the carbon dioxide passes through second amine scrubber zone 458 and into line 466. The amine may be regenerated which releases the hydrogen sulfide into line 460. Regenerated amine is then reused.

Yet another embodiment combines both of the above embodiments and calls for the first reaction zone to contain at least two stages with an interstage stream being heat exchanged with the stream introduced to the isomerization zone, and also calls for a portion of the first reaction zone product to be recycled to the first reaction zone and the first reaction zone product being heat exchanged with the stream introduced to the isomerization zone.

The invention claimed is:

1. A process for producing a branched paraffin-rich diesel boiling range product from a renewable feedstock comprising:
   a) treating the renewable feedstock in a first reaction zone by hydrogenating and deoxygenating the renewable feedstock using a catalyst at reaction conditions in the presence of hydrogen to provide a first reaction zone product stream comprising hydrogen, carbon dioxide, water, and n-paraffins wherein the first reaction zone comprises at least two stages connected by an interstage stream;
   b) separating, in a hot high pressure hydrogen stripper, a gaseous stream comprising hydrogen and at least a portion of the water and carbon oxides from the first reaction zone product stream c) and heat exchanging the remainder comprising at least the n-paraffins with the interstage stream;
   d) introducing the remainder stream, after heat exchange with the interstage stream, to a second reaction zone to contact an isomerization catalyst at isomerization conditions to isomerize at least the n-paraffins and generate a branched paraffin-rich stream;
   e) combining the branched paraffin-rich stream and the gaseous stream to form a combined stream;
   f) cooling the combined stream and separating a gaseous component comprising at least hydrogen and carbon dioxide from a liquid diesel boiling range component; and
   g) recovering the liquid diesel boiling range component.

2. The process of claim 1 wherein the first reaction zone additionally comprises at least a third stage connected to the second stage by a second interstage stream and the remainder stream is additionally heat exchanged with the second interstage stream.

3. The process of claim 1 further comprising removing at least a portion of the hydrogen from the branched paraffin-rich stream prior to combining the branched paraffin-rich stream and the gaseous stream.

4. The process of claim 3 further comprising recycling the hydrogen removed from the branched paraffin-rich stream to the hot high pressure hydrogen stripper.

5. The process of claim 1 further comprising separating at least carbon dioxide from the gaseous component stream and recycling the carbon dioxide depleted gaseous component stream to the first reaction zone.

6. The process of claim 1 further comprising recycling a portion of the remainder stream comprising a least the n-paraffins to the first reaction zone at a volume ratio of recycle to feedstock in the range of about 2:1 to about 8:1.

7. The process of claim 6 wherein the reaction conditions in the first reaction zone include a temperature of about 40° C. to about 400° C. and a pressure of about 689 kPa absolute (100 psia) to about 13,790 kPa absolute (2000 psia).

8. The process of claim 1 further comprising separating the liquid hydrocarbon component into an LPG and naphtha stream and a diesel boiling range stream and separating the LPG and naphtha stream into an LPG stream and a naphtha stream.

9. The process of claim 1 further comprising introducing a make up hydrogen stream to the hot high pressure hydrogen stripper.

10. The process of claim 1 wherein the isomerization conditions in the second reaction zone include a temperature of about 40° C. to about 400° C. and a pressure of about 689 kPa absolute (100 psia) to about 13,790 kPa absolute (2000 psia).

11. The process of claim 1 wherein the hot high pressure hydrogen stripper is operated at a temperature of about 40° C. to about 300° C. and a pressure of about 689 kPa absolute (100 psia) to about 13,790 kPa absolute (2000 psia).

12. The process of claim 1 wherein the second reaction zone is operated at a pressure at least 345 kPa absolute (50 psia) greater than that of the first reaction zone.

13. The process of claim 1 further comprising treating a petroleum derived feedstock in the first reaction zone with the renewable feedstock.

14. The process of claim 1 wherein the renewable feedstock comprises at least one component selected from the group consisting of canola oil, corn oil, soy oil, rapeseed oil, soybean oil, colza oil, tall oil, sunflower oil, hempseed oil, olive oil, linseed oil, coconut oil, castor oil, peanut oil, palm oil, mustard oil, cottonseed oil, inedible tallow, yellow and brown greases, lard, train oil, fats in milk, fish oil, algal oil, sewage sludge, ratanjoy oil, wild castor oil, jangli oil erandi oil, mohuwa oil, karanji honge oil, neem oil, and mixtures thereof.

15. The process of claim 1 wherein the renewable feedstock further comprises at least one co-feed component selected from the group consisting of spent motor oils, spent industrial lubricants, used paraffin waxes, liquids derived from the gasification of coal followed by a downstream liquefaction step, liquids derived from the gasification of biomass followed by a downstream liquefaction step, liquids derived from the gasification of natural gas followed by a downstream liquefaction step, liquids derived from depolymerization of waste plastics, synthetic oils, and mixtures thereof.

* * * * *